United States Patent
White (10) Patent No.: US 6,706,658 B2
(45) Date of Patent: Mar. 16, 2004

(54) CATALYST FOR PURIFICATION OF AROMATIC ACIDS

(75) Inventor: James Ferguson White, Twinsburg, OH (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 10/036,822

(22) Filed: Dec. 21, 2001

(65) Prior Publication Data

US 2003/0119665 A1 Jun. 26, 2003

(51) Int. Cl.[7] .......................... B01J 21/18; B01J 23/40; B28B 1/00; C01B 31/00; D01F 8/00
(52) U.S. Cl. .................... 502/182; 502/184; 502/185; 502/527.16; 502/527.24; 264/643; 264/29.1; 264/172.13; 264/176.1; 264/177.1; 264/177.16; 264/177.17
(58) Field of Search ................ 502/182, 184, 502/185, 527.16, 527.24; 264/643, 29.1, 172.13, 176.1, 177.1, 177.16, 177.17

(56) References Cited

U.S. PATENT DOCUMENTS

| | | | |
|---|---|---|---|
| 2,409,494 A | 10/1946 | Keating | 252/259.2 |
| 2,556,616 A | 6/1951 | Ellis | 258/27.5 |
| 2,611,750 A | 9/1952 | White | 260/2.5 |
| 3,084,394 A | 4/1963 | Bickerdike et al. | 18/54.7 |
| 3,109,712 A | 11/1963 | Redfern | 23/209.2 |
| 3,162,607 A | 12/1964 | Burbidge et al. | 252/477 |
| 3,171,720 A | 3/1965 | Shea, Jr. et al. | |
| 3,198,714 A | 8/1965 | Johnson et al. | 202/26 |
| 3,235,346 A | 2/1966 | Hucke | 29/190 |
| 3,288,475 A | 11/1966 | Benoit | 277/205 |
| 3,310,611 A | 3/1967 | Zocher | 264/5 |
| 3,342,555 A | 9/1967 | McMillan | 23/209.4 |
| 3,345,440 A | 10/1967 | Googin et al. | 264/29 |
| 3,348,967 A | 10/1967 | Hucke | 117/118 |
| 3,352,788 A | 11/1967 | Conlisk | 252/161 |
| 3,387,940 A | 6/1968 | McHenry et al. | 23/209.2 |
| 3,446,593 A | 5/1969 | Mostssd | 23/209.1 |
| 3,446,865 A | 5/1969 | Roth et al. | 260/669 |
| 3,544,502 A | 12/1970 | Boyer et al. | 260/29.7 |
| 3,565,980 A | 2/1971 | Otani | 264/29 |
| 3,574,548 A | 4/1971 | Sands et al. | 23/209.4 |
| 3,608,170 A | 9/1971 | Larson et al. | 29/149.5 |

(List continued on next page.)

FOREIGN PATENT DOCUMENTS

| | | |
|---|---|---|
| EP | 0 347 830 | 12/1989 |
| EP | 1 127 865 A1 | 8/2001 |
| EP | 1 205 241 A1 | 5/2002 |
| EP | 1 232 789 A1 | 8/2002 |
| WO | WO 01/08798 A1 | 2/2001 |
| WO | WO 01/21306 A1 | 3/2001 |

OTHER PUBLICATIONS

International Search Report, PCT/US02/39415, Apr. 17, 2003.

*Primary Examiner*—Elizabeth D. Wood
*Assistant Examiner*—Patricia L. Hailey
(74) *Attorney, Agent, or Firm*—Raymond F. Keller (57) ABSTRACT

One aspect of the invention relates to a catalyst composite containing an extruded catalyst support containing an extruded activated carbonaceous material having specifically a defined pore structure. For example, the extruded activated carbonaceous material may have pores wherein at least about 40% of total Hg porosity occurs in pores having a diameter of about 200 Å and larger. Alternatively the extruded activated carbonaceous material may have a first set of pores having a pore diameter of at least about 40 Å and at most about 100 Å with a porosity of at least about 0.15 cc/g, and a second set of pores having a pore diameter of at least about 5,000 Å and at most about 20,000 Å with a porosity of at least about 0.3 cc/g.

28 Claims, 2 Drawing Sheets

Pore Structure of cocoanut granular vs extruded carbon, via Hg Intrusion

Pore Diameter, Angstrom

U.S. PATENT DOCUMENTS

| | | | |
|---|---|---|---|
| 3,626,042 A | 12/1971 | Appleby et al. | 264/29 |
| 3,628,984 A | 12/1971 | Ishlkawa et al. | 117/46 |
| 3,634,569 A | 1/1972 | Emanuelson et al. | 264/105 |
| 3,635,676 A | 1/1972 | Sands | 23/209.4 |
| 3,657,166 A | 4/1972 | Caldwell | 260/2.5 |
| 3,663,171 A | 5/1972 | Granger | 23/209.1 |
| 3,775,078 A | 11/1973 | Elmer et al. | 65/32 |
| 3,859,421 A | 1/1975 | Hucke | 423/445 |
| 3,964,933 A | 6/1976 | Fung et al. | 136/121 |
| 4,029,567 A | 6/1977 | Farnand et al. | 208/8 |
| 4,052,336 A | 10/1977 | Van Montfoort et al. | |
| 4,061,596 A | 12/1977 | Matsushita et al. | 252/463 |
| 4,076,873 A | 2/1978 | Shea | 428/35 |
| 4,082,694 A | 4/1978 | Wennerberg et al. | 252/444 |
| 4,090,978 A | 5/1978 | Welsh et al. | 252/425.3 |
| 4,206,078 A | 6/1980 | Ohorodnik et al. | 252/423 |
| 4,263,268 A | 4/1981 | Knox et al. | 423/449 |
| 4,329,260 A | 5/1982 | Lester et al. | 252/446 |
| 4,399,052 A * | 8/1983 | Sugino | 252/421 |
| 4,552,976 A * | 11/1985 | Lin et al. | 560/204 |
| 4,603,119 A | 7/1986 | Karl et al. | 502/427 |
| 4,668,496 A | 5/1987 | Korb et al. | 423/445 |
| 4,892,972 A | 1/1990 | Schroeder et al. | 562/487 |
| 4,954,469 A | 9/1990 | Robinson | 502/80 |
| 4,987,116 A | 1/1991 | Karl et al. | 502/427 |
| 5,304,527 A | 4/1994 | Dimitri | 502/425 |
| 5,362,908 A | 11/1994 | Schroeder et al. | 562/487 |
| 5,538,932 A | 7/1996 | Yan et al. | 502/424 |
| 5,616,792 A | 4/1997 | Bartos et al. | 562/486 |
| 5,698,488 A * | 12/1997 | Birbara et al. | 502/325 |
| 5,726,118 A | 3/1998 | Ivey et al. | 502/417 |
| 5,756,833 A | 5/1998 | Rosen et al. | 562/486 |
| 5,773,657 A | 6/1998 | Rutter et al. | |
| 5,783,514 A * | 7/1998 | Schick et al. | 502/185 |
| 5,877,360 A | 3/1999 | Moore et al. | |
| 5,965,483 A | 10/1999 | Baker et al. | 502/425 |
| 6,024,899 A * | 2/2000 | Peng et al. | 264/29.1 |
| 6,177,380 B1 * | 1/2001 | Zoeller et al. | 502/181 |
| 6,417,133 B1 * | 7/2002 | Ebner et al. | 502/185 |

* cited by examiner

CATALYST FOR PURIFICATION OF AROMATIC ACIDS

FIELD OF THE INVENTION

The present invention generally relates to catalyst composites containing extruded catalyst supports, and methods of making and employing the catalyst composites. The present invention particularly relates to catalyst materials and methods associated with the purification of terephthalic acid.

BACKGROUND OF THE INVENTION

Catalytic processes are indispensable in the chemical industry. Frequently, catalytic processes employ a catalyst that is incorporated on a support. Effective use of the catalyst often corresponds to the quality of the catalyst support. Poor quality catalyst supports, due to at least one of physical degradation, chemical degradation, undesirable properties, and inconsistent properties, limit the effectiveness of catalysts incorporated therein. Conditions such as high temperatures, high pressures, and high or low pH environments present challenges to the integrity of catalyst supports.

For example, conventional catalyst composites for the purification of terephthalic acid by the Amoco mid-continent process (PTA catalysts) are composed of palladium-supported on granular 4×8 mesh carbon. These catalyst composites are designed to remove the two major impurities present in crude terephtahlic acid; namely yellow color and 4-carboxy benzaldehyde (4-CBA).

Carbon is the preferred support material for conventional PTA catalysts because it is essentially the only readily available material that can simultaneously yield an effective catalyst for color removal, 4-carboxy benzaldehyde removal, and also withstand the extremely corrosive environment of the terephthalic acid purification process. Although conventional carbon supported PTA catalysts have been used extensively over the past 20 years, such catalyst composites suffer from several disadvantages. These disadvantages include: highly irregular shapes leading to possible mal-distribution of liquid or gas flows in a catalytic reactor bed utilizing such catalyst composites; irregular shapes having sharp and fragile edges and corners which tend to break off and contaminate the PTA product with undesirable dust and black particles; brittleness which also leads to breakage and dust/black particles contaminating the PTA product; natural origin, i.e., coconut shell, which leads to non-uniformity form one growing season to another and consequent non-consistency of the carbon support; and being commonly derived from nutshells, such activated carbon is highly microporous, leading to the requirement of locating all of the active catalytic metal at the surface of the particles, where it is undesirably susceptible to loss during the movement and abrasion which occurs during shipping and handling.

Particularly problematic is the unpredictable and uncontrollable melange of irregular shapes and sizes associated with commonly employed granular cocoanut carbon supports. Granular cocoanut carbons are also mostly microporous; that is, they have numerous pores having a pore diameter less than 50 Å. As a result, the catalytic metals must be located near the exterior edges of the supports to avoid low activity due to mass transfer resistances. However, when catalytic metals are located near the exterior edges of supports, they are subject to loss due to mechanical attrition and thus the catalyst support loses its activity. Catalytic metals located near the exterior edges of a support are readily accessible to corrosion metals commonly present in reactor feeds and thus subject to deactivation.

Non-carbon catalyst supports are employed in catalytic processes in attempts to overcome the disadvantages associated with conventional carbon supported catalysts. Non-carbon supports include alumina supports, silica supports, alumina-silica supports, various clay supports, titania, and zirconium supports. However, there are at least one of two disadvantages associated with non-carbon catalyst supports; namely, that they may become weak and loose physical strength, that they are dissolved in highly corrosive environments (such as hot aqueous solutions of terephthalic acid) and that they have difficulties in removing undesirable color from crude terephthalic acid.

Improved catalyst supports and catalyst composites are therefore desired. Specifically, improved PTA catalyst supports and PTA catalyst composites are desired to provide improved methods of purifying terephthalic acid and improved useful lifetimes.

SUMMARY OF THE INVENTION

The present invention is designed to address at least one of and preferably all of the above disadvantages by providing a catalyst composite containing a composite support which is formed into shapes with mesoporosity and macroporosity. The catalyst composites of the present invention enjoy an extended useful lifetime compared to conventional catalyst composites since they contain a support composed of an extruded carbonaceous material capable of withstanding harsh, corrosive reaction environments, such as those encountered in PTA catalysis. In this connection, the catalyst composites of the present invention have a lower deactivation rate than conventional catalyst composites. The catalyst composites of the present invention also enjoy the same or better activity with about 30% to about 50% by weight less active metal compared to conventional catalyst composites.

One aspect of the invention relates to a catalyst composite containing a metal catalyst and an extruded catalyst support containing an extruded activated carbonaceous material having specifically a defined pore structure. For example, the extruded activated carbonaceous material may have pores wherein at least about 40% of total Hg porosity occurs in pores having a diameter of about 200 Å or larger. Alternatively the extruded activated carbonaceous material may have a first set of pores having a pore diameter of at least about 40 Å and at most about 100 Å with a porosity of at least about 0.15 cc/g, and a second set of pores having a pore diameter of at least about 5,000 Å and at most about 20,000 Å with a porosity of at least about 0.3 cc/g.

Another aspect of the invention relates to a method of making a catalyst composite involving mixing at least one carbonaceous material and a liquid to form a mixture; extruding the mixture into a shaped material; optionally drying the shaped material; heat treating the shaped material at a temperature from about 600° C. to about 1,500° C. to provide a catalyst support, wherein the catalyst support has at least one of the two to four specifically a defined pore structures, and contacting a precious metal catalyst with the catalyst support.

Yet another aspect of the invention relates to a method of purifying a crude polycarboxylic aromatic acid composition involving contacting the crude polycarboxylic aromatic acid composition with a catalyst composite containing a metal catalyst and an extruded activated carbonaceous material having at least one of the two to four specifically a defined pore structures. And still yet another aspect of the invention relates to a method of purifying a crude amine composition or a crude alkynol amine composition involving contacting the crude amine composition or the crude alkynol amine composition with a catalyst composite containing a catalyst support containing a metal catalyst and an extruded activated carbonaceous material having at least one of the two to four specifically a defined pore structures.

DETAILED DESCRIPTION OF THE INVENTION

In one embodiment, the present invention involves the preparation of catalyst composites containing an extruded carbon catalyst support. The extruded catalyst support is particularly suited for metal catalysts, especially palladium or platinum. The process according to the present invention of preparing the extruded catalyst support may involve the mixing of a carbonaceous material and optional additives. A liquid is preferably added to the mix to give a stiff dough which is then extruded (or pelletized or spheridized), optionally dried and heat treated to provide a material having at least one of two pore structures. After heat treatment of the extruded and optionally dried material, impregnation with an active metal catalyst is conducted. In another embodiment, the present invention involves the use of a catalyst composite in a catalytic process, such as in the purification of crude terephthalic acid.

The extruded carbon catalyst support contains a carbonaceous material, and optionally one or more additives. The carbonaceous material may be derived from any suitable carbon source. The carbonaceous material initially used is an activated carbon, or a non-activated carbon that may be converted to activated carbon at some point during the formation of the extruded carbon catalyst support. For example, charcoal (a non-activated carbonaceous material) may be converted to activated carbon during the heat treatment step (subsequently described). Carbonaceous materials include activated carbon derived from coal, lignite, wood, nutshells, peat, pitches, cokes, and the like; and non-activated carbon derived from carbon char powder (e.g. charcoal).

The carbonaceous material combined with any optional additives is typically in powder form. In one embodiment, the carbonaceous material has a particle size (average particle size) of less than about 100 microns. In another embodiment, the carbonaceous material has a particle size of less than about 80 microns. In yet another embodiment, the carbonaceous material has a particle size of less than about 50 microns. In still yet another embodiment, the carbonaceous material has a particle size of less than about 25 microns.

Carbonaceous materials are commercially available or they may be made. For example, carbonaceous materials may be derived from coal, coke, coal coke, petroleum coke, lignite, polymeric materials, graphite, bone, wood, nut shells including coconut shells, resin wastes, lignocellulosic materials including pulp and paper, kernel, fruit pits, and sugar. The source of carbonaceous materials is not critical to the present invention. Consequently, another advantage associated with the present invention is that the source of carbonaceous materials is not critical. U.S. Pat. Nos. 3,084,394; 3,109,712; 3,171,720; 3,198,714; 3,310,611; 3,387,940; 3,342,555; 3,345,440; 3,352,788; 3,446,593; 3,565,980; 3,574,548; 3,626,042; 3,628,984; 3,634,569; 3,635,676; 3,663,171; 3,859,421; 4,029,567; 4,082,694; 4,206,078; 4,263,268; 4,329,260; 4,603,119; 4,668,496; 4,954,469; 4,987,116; describe various carbonaceous materials and are hereby incorporated by reference in this regard.

The carbonaceous materials are chemically activated or non-chemically activated. Chemical activating agents include one or more of alkali metal hydroxides, alkali metal carbonates, alkali metal sulfide, alkali metal sulfates, alkaline earth metal carbonates, alkaline earth metal chlorides, alkaline earth metal sulfates, alkaline earth metal phosphates, phosphoric acid, polyphosphoric acid, pyrophosphoric acid, zinc, chloride, sulfuric acid, and the like. Chemical activation is conducted by contacting one or more carbonaceous materials with one or more chemical activating agents, mixing, optionally heating, optionally washing/rinsing, and optionally drying the chemically activated material.

In one embodiment, the extruded carbon catalyst support contains about 50% by weight or more and about 100% by weight or less of at least one carbonaceous material. In another embodiment, the extruded carbon catalyst support contains about 60% by weight or more and about 99.9% by weight or less of at least one carbonaceous material. In yet another embodiment, the extruded carbon catalyst support contains about 70% by weight or more and about 99% by weight or less of at least one carbonaceous material. In still yet another embodiment, the extruded carbon catalyst support contains about 75% by weight or more and about 95% by weight or less of at least one carbonaceous material.

Extruded carbon catalyst supports are commercially available. For example, extruded carbon materials are available from Ceca, Norit, Westvaco, and Takeda. Alternatively, the extruded carbon catalyst support may be made by mixing the carbonaceous material and any optional additives, forming the mixture into a shaped material, optionally drying the shaped material, and heat treating the shaped material to provide the hard, extruded carbon catalyst support. When mixing the carbonaceous material and any optional additives, it is preferable to add water (and/or other liquid solvent). Tap water or deionized water may be employed, but deionized water is preferred. Water is added to facilitate mixing and subsequent forming (for instance, extrusion), and thus it is added in any amount suitable to facilitate mixing and subsequent forming. Since water is eventually removed in subsequent drying and heat treatment steps, the amount of water added is not critical to the present invention.

Nevertheless, in one embodiment, the mixture of optional additives and carbonaceous material typically contains from about 5% to about 80% by weight water. In another embodiment, the mixture of optional additives and carbonaceous material contains from about 10% to about 70% by weight water. In another embodiment, the mixture of optional additives and carbonaceous material contains from about 20% to about 60% by weight water.

Additives include any material that facilitates mixing and subsequent forming. Additives include rheology control agents, extrusion aids, suspension agents, surfactants, low boiling organic compounds, rosin materials, polymeric additives, dispersing agents such as ammonium lignosulfonates, and metal nitrates, sulfates, carbonates, phosphates, hydroxides, and oxides. Rheology control agents include cellulose ethers, polyvinyl alcohols, and polyalkylene oxides. Examples of cellulose ethers include sodium carboxymethylcellulose (CMC), hydroxyethylcellulose (HEC), methylcellulose (MC) and derivatives thereof. One commercially available cellulose ether is Methocel. Methocel, which contains water and hydroxypropylmethylcellulose ether polymer, has a high thermal gelatin point, such as the products designated as K4M and K15M available from Dow Chemical Company. Preferred polyalkylene oxides include polyethylene oxides. Extrusion aids include glycol compounds, such as polyalkylene glycols. In a specific embodiment, polyethylene glycol, such as PEG 400 available from Union Carbide can be added as an extrusion aid. Generally, the glycol compounds are dissolved in water and then added to the dry ingredients.

In one embodiment, the extruded carbon catalyst support typically contains from about 0.01% to about 10% by weight of at least one additive. In another embodiment, the extruded carbon catalyst support contains from about 0.1% to about 5% by weight of at least one additive.

The mixture of carbonaceous powder and any optional ingredients may be mixed well in a high shear mixer with water and a rheology control agent, such as Methocel until a rather stiff dough is obtained. This dough can be extruded and formed into any suitable shape including cylinders, cubes, stars, tri-lobes, quadra-lobes, pellets, spheres by suitable mechanical means. In one embodiment, mixing is conducted in a high intensity environment, such as that supplied by a Littleford Mixer available from Littleford Day, Inc., Florence, Ky. Mixing is conducted for a time sufficient so that a fine uniform mix results. In another embodiment, deionized water is added to the mixture during mixing in an amount to yield a stiff, dough-like material suitable for extrusion.

In one embodiment, the mixture of carbonaceous material and optional additives is mixed in a high intensity mixer from about 5 minutes to about 100 minutes. In another embodiment, mixture of carbonaceous material and optional additives is mixed in a high intensity mixer from about 10 minutes to about 60 minutes. In yet another embodiment, mixture of carbonaceous material and optional additives is mixed in a high intensity mixer from about 15 minutes to about 40 minutes.

After mixing, the mixed material is extruded into a suitable shape. The shape substantially corresponds to the shape of the resultant catalyst support. In a preferred embodiment, the mixed material is extruded in a continuous manner over a broad range of diameters and shapes. Examples of forming or extrusion machines include extrusion molding machines, single screw extruders, twin screw extruders, coextruders, pin extruders, linear extruders, and monofilament extruders.

The extruded material is then optionally formed into any desired shape. Examples of forming machines include molding machines, tableting machines, rolling granulators, marumarizers, and pelletors. The shape of the extruded material includes spheres, tablets, cylinders, stars, tri-lobes, quadra-lobes, pellets, granules, honeycombs, and cubes. The shapes, generally referred to as "particulate", may have any suitable size. However, in a preferred embodiment, the sizes of the shapes are substantially uniform. In another preferred embodiment, the mixed material is extruded into cylindrical shapes having diameters from about 1.5 mm to about 3.5 mm.

The extruded material has its components (the carbonaceous material and any optional additives) uniformly mixed therein. Uniformly mixed optional additives and carbonaceous material in the subsequent resultant catalyst support contributes to the advantageous properties of the resultant extruded catalyst support and resultant catalyst composite containing the catalyst support.

After extruding the material into a desired shape, the extruded material is optionally dried to remove any remaining liquid (and typically to remove remaining water). Drying is conducted in at least one of a desiccator, under a vacuum (reduced pressure), and/or elevated temperature (baking) for a sufficient period of time to remove any remaining liquid from the formed material. Drying the extruded material contributes to the attrition resistance properties of the resultant extruded carbon catalyst support.

The manner in which the extruded material is dried is not critical, but in many instances the drying conditions primarily depend upon at least one of the dimensions of the extruded material, the shape of the extruded material and the manner in which the extruded material is held. In one embodiment, the dried extruded material contains less than about 3% by weight free moisture. In another embodiment, the dried extruded material contains less than about 1% by weight free moisture. In yet another embodiment, the dried extruded material contains less than about 0.5% by weight free moisture.

In one embodiment, drying involves at least one of maintaining an elevated temperature (above about 35° C.) overnight, desiccation overnight, and under a vacuum overnight. When employing elevated temperatures, in one embodiment, the extruded material is heated from about 35° C. to about 150° C. for a time from about 5 seconds to about 6 hours. In another embodiment, the extruded material is heated from about 40° C. to about 110° C. for a time from about 30 seconds to about 30 minutes. In yet another embodiment, the extruded material is heated from about 50° C. to about 90° C. for a time from about 1 minute to about 20 minutes. In a preferred embodiment, the extruded material is subjected to a ramped drying process (two step drying process), with the initial drying temperature from about 40° C. to about 95° C., and more preferably from about 60° C. to about 85° C., and then heated to at least about 100° C., and more preferably at least about 110° C., to complete the drying process.

After drying, the extruded material is heat treated. However, in one embodiment, the drying step may be incorporated into the heat treatment step by starting the heat treatment at a relatively low temperature (low temperatures relative to the heat treatment temperatures). The dried and extruded material is heat treated in any suitable manner to provide a hard catalyst support and to provide a catalyst support containing a carbonaceous material having properties corresponding with those of activated carbon (especially in embodiments where a non-activated carbonaceous material is employed).

In one embodiment, heat treatment involves heating the extruded material at a temperature from about 600° C. to about 1,500° C. In another embodiment, heat treatment involves heating the extruded material at a temperature from about 700° C. to about 1,000° C. In yet another embodiment, heat treatment involves heating the extruded material at a temperature from about 800° C. to about 900° C. It is noted that the temperature may vary within a temperature range. For example, the temperature may be ramped or steadily increased during the length of the heat treatment.

The length of time the extruded material is heated primarily depends upon the temperature, the contents of atmosphere, the size of the extruded material, the related equipment, and the identity of the components (the specific type of carbonaceous material and the optional additives). In one embodiment, heat treatment involves heating the extruded material from about 15 minutes to about 5 hours. In another embodiment, heat treatment involves heating the extruded material from about 30 minutes to about 4 hours. Heating time refers to the amount of time that the extruded material itself is at the temperature specified (and thus does not include ramping up or cooling down).

In one embodiment, the atmosphere in which the heat treatment is conducted contains at least steam or water vapor. The atmosphere may further contain at least one of an inert gas, air, oxygen, and carbon dioxide. Inert gases include the noble gases and nitrogen. Noble gases include helium, neon, argon, krypton, and xenon. In another embodiment, the atmosphere in which the heat treatment is conducted contains at least one of steam/water vapor and an inert gas. In this connection, in one embodiment, the heat treatment atmosphere contains a substantially inert atmosphere, such as from about 50% to about 100% of at least one an inert gas and from about 0% to less than about 50% of one or more of steam, air, oxygen, and carbon dioxide. In a preferred embodiment, the heat treatment atmosphere contains steam and nitrogen.

In one embodiment, the heat treatment atmosphere contains from about 5% to about 100% steam and from 0% to about 95% of at least one of an inert gas, air, oxygen, and carbon dioxide. In another embodiment, the heat treatment atmosphere contains from about 20% to about 95% steam and from about 5% to about 80% of at least one of an inert gas, air, oxygen, and carbon dioxide. In yet another embodiment, the heat treatment atmosphere contains from about 30% to about 90% steam and from about 10% to about 70% of at least one of an inert gas, air, oxygen, and carbon dioxide.

After heat treatment, the optionally dried, extruded product is cooled in any suitable manner. In one embodiment, the optionally dried, extruded product is cooled under an atmosphere containing an inert gas.

The resultant extruded carbon catalyst supports of the present invention possess a level of porosity is that controllable, primarily by varying the heat treatment parameters and by varying the relative amounts of the ingredients (the carbonaceous material and the optional additives). Porosity may also be controllable or is further controllable by the amount and the type of additive, such as the rheology control agent or the extrusion aid.

In one embodiment, the extruded carbon catalyst supports of the present invention have a bulk density from about 400 grams per liter to about 1,000 grams per liter. In another embodiment, the extruded carbon catalyst supports have a bulk density from about 425 grams per liter to about 750 grams per liter. In yet another embodiment, the extruded carbon catalyst supports have a bulk density from about 440 grams per liter to about 600 grams per liter.

Generally, the surface area of the extruded carbon catalyst supports of the present invention correspond to a weighted average of the surface area of the optional additives and carbonaceous material. In one embodiment, the surface area of the extruded carbon catalyst supports is about 300 $m^2/g$ or more and about 1,600 $m^2/g$ or less. In another embodiment, the surface area of the extruded carbon catalyst supports is about 800 $m^2/g$ or more and about 1,400 $m^2/g$ or less.

The extruded carbon catalyst supports generally have a unique distribution of pore sizes that contributes to the advantages obtained by the present invention. While not wishing to be bound by any theory, it is believed that the minimum surface area and/or distribution of pore sizes in extruded carbon catalyst supports of the present invention contributes to improved aging (by maximizing porosity in pore sizes of about 200 Å or larger, such as at least about 40% porosity in pore sizes of about 200 Å or larger or at least about 38% porosity in pore sizes of about 1,000 Å or larger); improved HMBA/toluic acid ratios; improved CBA removal and/or improved yellow color removal.

In one embodiment, the extruded carbon catalyst has a pore size distribution wherein a first set of pores containing a porosity of at least about 0.15 cc/g have a pore diameter of at least about 40 Å and at most about 100 Å, and a second set of pores containing a porosity of at least about 0.3 cc/g have a pore diameter of at least about 5,000 Å and at most about 20,000 Å (Hg intrusion porosimetry, such as using a Micromeritics model AutoPore-II 9220 porosimeter in accordance with the analysis method outlined in one or more of U.S. Pat. Nos. 5,186,746; 5,316,576; and 5,591,256). In another embodiment, the extruded carbon catalyst has a pore size distribution wherein a first set of pores containing a porosity of at least about 0.2 cc/g have a pore diameter of at least about 40 Å and at most about 100 Å, and a second set of pores containing a porosity of at least about 0.4 cc/g have a pore diameter of at least about 5,000 Å and at most about 20,000 Å.

Figure 1:
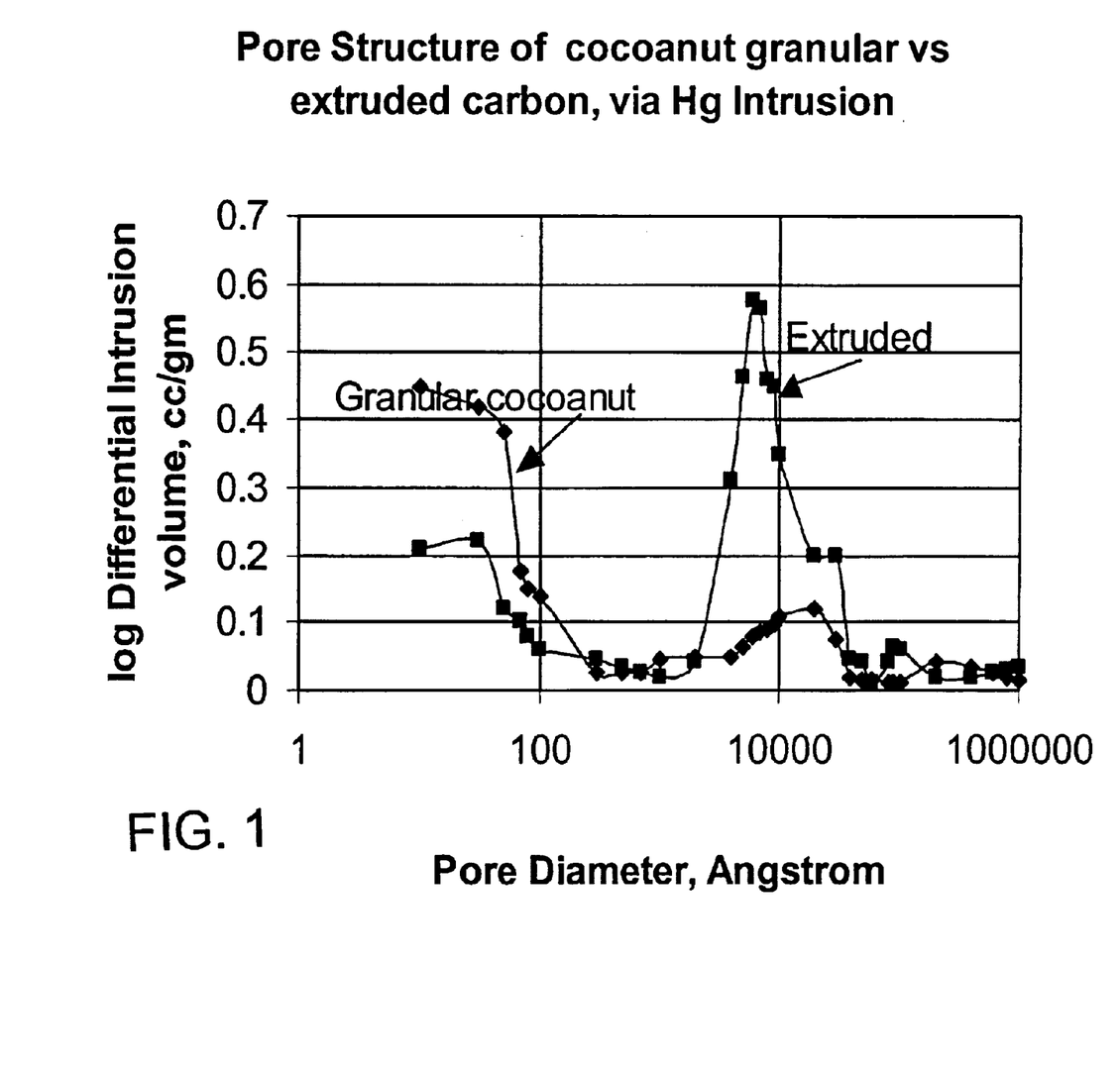
FIG. 1 shows a graph of pore diameter distribution of conventional granular carbon and extruded carbon in accordance with one aspect of the present invention.

Referring to FIG. 1, the pore structure of a typical, conventional granular coconut carbon (Pica G202X) is compared with an extruded carbon (Takeda S2X) in accordance with one embodiment of the present invention. The pore volume distribution of the extruded carbon in accordance with the present invention is weighted much more heavily in larger pores whereas the conventional granular coconut carbon is weighted in relatively small pores. For this reason, the conventional granular coconut carbon is referred to as microporous, whereas the extruded carbon in accordance with the present invention may be referred to mesoporous and macroporous.

Figure 2:
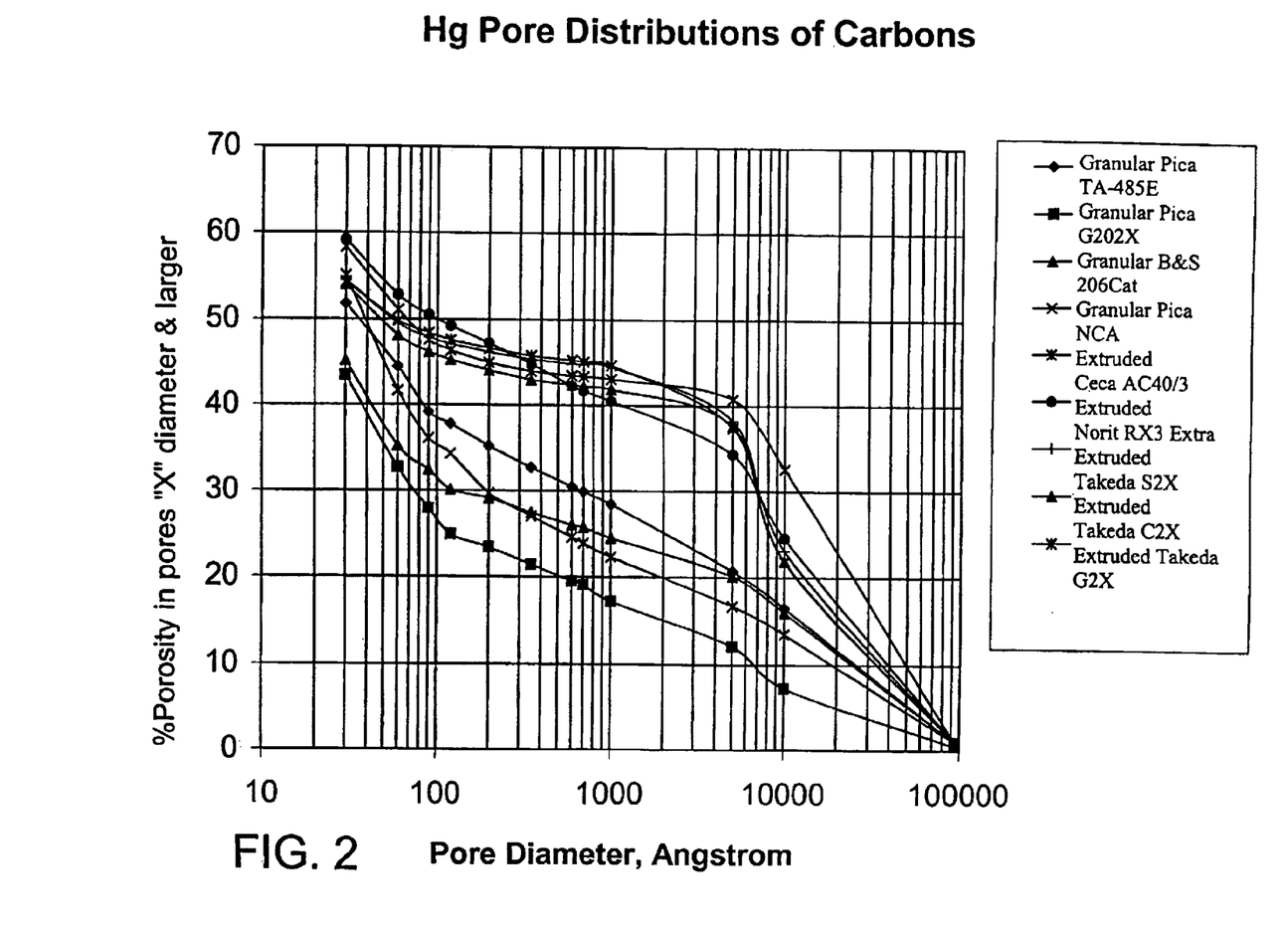
FIG. 2 shows a graph of pore diameter distribution of several conventional granular carbons and several embodiments of extruded carbon in accordance with one aspect of the present invention.

Referring to FIG. 2, the pore structure of four typical, conventional granular coconut carbons are compared with five different embodiments of the extruded carbons in accordance with the present invention. In the graph, conventional granular coconut carbons include Granular TA-485E available from Pica, Granular G202X available from Pica, Granular 206CAT available from Barneby-Waterlink, and Granular NCA available from Pica. Extruded carbons include Extruded AC40/3 available from Ceca, Extruded RX3 Extra available from Norit, Extruded S2X available from Takeda, Extruded G2X available from Takeda, and Extruded C2X available from Takeda. The pore volume distribution of the extruded carbons in accordance with the present invention is weighted much more heavily in larger pores whereas the conventional granular coconut carbon is weighted in relatively small pores. For example, as seen from the graph, at least about 40% of total Hg porosity occurs in pores having a diameter of about 200 Å and larger, such as about 1,000 Å and larger.

In Table 1 below, the amount (% by weight) of palladium in a catalyst composite and corresponding 4-CBA removal rates are reported. The 4-CBA removal rate is the ratio of the first order 4-CBA removal rate for the subject catalyst composite divided by the first order 4-CBA removal rate for a conventional standard catalyst composite (catalyst composite containing a Pica G202X support). The catalyst composites according to the present invention (containing the Takeda C2X or Ceca AC40/3 based composite) exhibit improved 4-CBA removal rates compared to a standard catalyst composite (catalyst composite containing a Pica G202X support).

TABLE 1

| catalyst support | % Pd | 4-CBA removal rate |
|---|---|---|
| Takeda C2X | 0.5 | 1.25 |
| Takeda C2X | 0.35 | 1.11 |
| Takeda C2X | 0.25 | 0.95 |
| Ceca AC40/3 | 0.5 | 1.2 |
| Ceca AC40/3 | 0.35 | 1.15 |
| Pica G202X | 0.5 | 1.0 |

In one embodiment, the extruded carbon catalyst has a pore size distribution wherein at least about 40% of total Hg porosity occurs in pores having a diameter of about 200 Å and larger (Hg intrusion porosimetry). In another embodiment, the extruded carbon catalyst has a pore size distribution wherein at least about 38% of total Hg porosity occurs in pores having a diameter of about 1,000 Å and larger. In yet another embodiment, the extruded carbon catalyst has a pore size distribution wherein at least about 34% of total Hg porosity occurs in pores having a diameter of about 5,000 Å and larger.

In one embodiment, the extruded carbon catalyst has an HMBA/toluic acid ratio at the end of a run of at least about 2.5. The HMBA/toluic acid ratio at the end of a run is the ratio of 4-hydroxymethyl benzoic acid to toluic acid present at the end of a test purification reaction (in the feed, the HMBA/toluic acid ratio is about 0.44). In another embodiment, the extruded carbon catalyst has an HMBA/toluic acid ratio at the end of a run of at least about 2.75. In yet another embodiment, the extruded carbon catalyst has an HMBA/toluic acid ratio at the end of a run of at least about 3. In still yet another embodiment, the extruded carbon catalyst has an HMBA/toluic acid ratio at the end of a run of at least about 3.25.

The extruded carbon catalysts of the present invention generally have a longer life compared to a conventional granular carbon catalysts. In other words, the extruded carbon catalysts of the present invention generally have a lower deactivation rate than conventional granular carbon catalysts. For example, in one embodiment, the extruded carbon catalyst of the present invention containing 0.5% by weight metal catalyst has about a 1.5 times or more longer life than a conventional granular carbon catalyst containing 0.5% by weight of the same metal catalyst. In another embodiment, the extruded carbon catalyst of the present invention containing 0.5% by weight metal catalyst has about a 2 times or more longer life than a conventional granular carbon catalyst containing 0.5% by weight of the same metal catalyst.

In yet another embodiment, the extruded carbon catalyst of the present invention has a deactivation rate that is about 25% or more lower than the deactivation rate of a similarly loaded (same amount of same metal catalyst) conventional granular carbon catalyst. In still yet another embodiment, the extruded carbon catalyst of the present invention has a deactivation rate that is about 50% or more lower than the deactivation rate of a similarly loaded conventional granular carbon catalyst.

Since the extruded carbon catalysts of the present invention have a lower deactivation rate than similarly loaded conventional granular carbon catalysts, the activities of the extruded carbon catalysts of the present invention are higher after various levels of aging compared to conventional granular carbon catalysts. In one embodiment, the extruded carbon catalyst of the present invention has an activity that is at least about 1.5 times higher than a similarly loaded conventional granular carbon catalyst after 6 months, 12 months, or 18 months of aging. In another embodiment, the extruded carbon catalyst of the present invention has an activity that is at least about 2 times higher than a similarly loaded conventional granular carbon catalyst after 6 months, 12 months, or 18 months of aging.

The extruded carbon catalysts of the present invention with low metal loading generally can perform equal to or even better than a conventional granular carbon catalysts with high metal loading. For example, in one embodiment, the extruded carbon catalyst of the present invention containing 0.25% by weight metal catalyst has an activity equal to or higher than a conventional granular carbon catalyst containing 0.5% by weight of the same metal catalyst. In another embodiment, the extruded carbon catalyst of the present invention containing 0.35% by weight metal catalyst has an activity equal to or higher than a conventional granular carbon catalyst containing 0.5% by weight of the same metal catalyst.

In one embodiment, the present invention involves forming a catalytic composite by impregnating the extruded carbon catalyst support with a solution of at least one catalytically active metal. The impregnation is effected by treating the extruded carbon catalyst support with an aqueous or organic solution of the desired metal or combination of metals in an amount sufficient to deposit at least one catalytically active metal on or near the surface of the support, thereby providing a catalyst composite.

Catalytically active metals typically include precious metals. Examples of catalytically active metals and mixture of metals include platinum, platinum and rhenium, platinum and ruthenium, platinum and tungsten, platinum and nickel, platinum and tin, platinum and iron, platinum and copper, platinum and rhodium, platinum and lead, platinum and germanium, platinum and gold, platinum and tellurium, palladium and gold, palladium and indium, palladium and sulfur, palladium and tellurium, palladium, palladium and rhenium, palladium and rhodium, palladium and tungsten, palladium and nickel, palladium and tin, palladium and copper, palladium and ruthenium, palladium and lead, palladium and germanium, cobalt, rhodium, ruthenium, osmium, iridium, various combinations thereof, etc. It is to be understood that the aforementioned list of catalytically active metals are only representative, and thus not limiting of the type of metals which may be impregnated on the catalytic support surface.

The catalyst may be impregnated onto/into the extruded carbon catalyst support in any suitable manner. For example, immersion techniques, spraying techniques, and incipient wetness techniques may be employed. In one embodiment, the amount of catalyst in the catalyst composite is from about 0.01% to about 30% by weight. In another embodiment, the amount of catalyst in the catalyst composite is from about 0.1% to about 10% by weight. In yet another embodiment, the amount of catalyst in the catalyst composite is from about 0.2% to about 5% by weight. In one embodiment, the amount of the extruded carbon catalyst support in the catalyst composite is from about 70% to about 99.99% by weight. In another embodiment, the amount of the extruded carbon catalyst support in the catalyst composite is from about 90% to about 99.9% by weight. In yet another embodiment, the amount of the extruded carbon catalyst support in the catalyst composite is from about 95% to about 99.8% by weight.

The extruded carbon catalyst supports and catalyst composites of the present invention are suitable for use in catalytic processes. Catalytic processes where the extruded carbon catalyst supports and catalyst composites of the present invention can be employed include hydrogenation, rearrangement, purification, dehydration, dehydrogenation, oxidation, reduction, polymerization, dehydrocylcization, reforming, hydrocracking, and isomerization. The specific catalytic reactions/processes are too numerous to list, but the following are specific examples.

The extruded catalyst composite of the present invention is suitable for use in purification of relatively impure or crude polycarboxylic aromatic acids, particularly crude terephthalic acid, isophthalic acid, phthalic acid and naphthalene dicarboxylic acid. The extruded catalyst composite of the present invention is also suitable for use in purification of amines and alkynol amines, and particularly aromatic amines, aromatic alkynol amines, aliphatic amines, and aliphatic alkynol amines.

In one embodiment, the impure polycarboxylic aromatic acid is a crude product of the catalytic oxidation of an aromatic compound. Examples of suitable aromatic compounds include 1,2-dimethylnaphthalene; 2,6-dialkylnaphthalene; 2-acyl-6-alkylnaphthalene; 2,6-dimethylnaphthalene, 2,6-diethylnaphthalene; 2,6-diisopropylnaphthalene; 2-acetyl-6-methylnaphthalene; 2-methyl-6-ethyl naphthalene; para-dialkylxylene; meta-dialkylxylene; and ortho-dialkylxylene; wherein the alkyl groups contain from 1 to about 6 carbon atoms. In a preferred embodiment, the crude acid purified in accordance with the present invention is at least one of terephthalic acid formed by the oxidation of para-xylene, isophthalic acid formed by the oxidation of meta-xylene and 2,6-naphthalene dicarboxylic acid formed by the oxidation of 2,6-dialkylnaphthalene (preferably 2,6-dimethyl naphthalene). In another embodiment, the crude polycarboxylic aromatic acid, such as 2,6-naphthalene dicarboxylic acid, is made by esterification to form the corresponding ester, in this case dimethyl naphthalene dicarboxylate, and then hydrolyzation to form the polycarboxylic aromatic acid which is then purified in accordance with the present invention.

Methods of catalytically purifying crude polycarboxylic aromatic acids including terephthalic acid are known. For example, U.S. Pat. Nos. 3,607,921; 3,887,613; 3,919,306; 4,260,817; 4,281,179; 4,317,923; 4,394,299; 4,415,479; 4,447,646; 4,605,763; 4,629,715; 4,791,226; 4,803,295; 4,808,751; 4,892,972; 4,937,378; 5,180,849; 5,362,908; 5,420,344; 5,616,792; 5,723,659; 5,756,833; describe various methods of catalytically purifying crude polycarboxylic aromatic acids and particularly terephthalic acid and are hereby incorporated by reference for their teachings in this regard. Methods of catalytically purifying crude amines and alkynol amines, and particularly aromatic amines and aromatic alkynol amines, are known. In this connection, the catalyst composite according to the present invention may be used in such methods.

In one embodiment, the catalyst composite is contacted with an aqueous solution or relatively impure or crude terephthalic acid that includes relatively large amounts of impurities such as 4-carboxy benzaldehyde and undesirable coloring. Such impurities are typically present in amounts up to about 10,000 parts per million parts of terephthalic acid, by weight (although higher amounts are encountered in some instances). These impurities adversely affect subsequent terephthalic acid polymerization reactions to produce polyethylene terephthalate, as well as cause undesirable coloring of the resulting polyethyleneterephthalate polymers.

In this embodiment, the catalyst composite is contacted with an aqueous solution of relatively impure or crude terephthalic acid at an elevated temperature and pressure in a fixed catalyst bed. The crude terephthalic acid to be purified is dissolved in water or a like polar solvent. Water is a preferred solvent; however, other suitable polar solvents include the relatively lower molecular weight alkyl carboxylic acids, alone or admixed with water.

In one embodiment, the temperature during catalytic purification is from about 100° C. to about 350° C. In another embodiment, the temperature during catalytic purification is from about 225° C. to about 340° C.

The pressure primarily depends upon the temperature at which the purification process is carried out. Inasmuch as the temperatures at which practical amounts of the impure terephthalic acid may be dissolved are substantially above the normal boiling point of the polar solvent, the pressures are necessarily considerably above atmospheric pressure to maintain the aqueous solution in liquid phase. If the reactor is hydraulically full, the reactor pressure can be controlled by the feed pumping rate. In one embodiment, the pressure during hydrogenation is from about 150 pounds per square inch guage (psig) to about 1600 psig. In another embodiment, the pressure during hydrogenation is from about 900 psig to about 1,200 psig.

In the operating mode where process control is effected by adjusting the hydrogen partial pressure, the hydrogen partial pressure in the reactor preferably is from about 10 psig to about 800 psig, from about 100 psig to about 600 psig, or higher, depending upon the service pressure rating of the reactor, the degree of contamination of the impure terephthalic acid, the activity and age of the particular catalyst employed, and like processing considerations. When purifying impure or crude terephthalic acid, in one embodiment, the reactor atmosphere contains from about 10% to about 40% by weight hydrogen and from about 60% to about 90% by weight water vapor. In another embodiment, when purifying impure or crude terephthalic acid, the reactor atmosphere contains from about 15% to about 35% by weight hydrogen and from about 65% to about 85% by weight water vapor.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, an amount of hydrogen that is sufficient to effect the desired hydrogenation under the reaction conditions employed is supplied to the purification reactor.

In one embodiment, activity rates for the removal of 4-carboxy benzaldehyde with a 0.5% by weight Pd catalyst composites (made of Pd on the extruded carbon catalyst supports) of the present invention are from about 1 hr$^{-1}$ to about 2.6 hr$^{-1}$. In another embodiment, activity rates for the removal of 4-carboxy benzaldehyde with a 0.5% by weight Pd catalyst composites of the present invention are from about 1.1 hr$^{-1}$ to about 2.2 hr$^{-1}$.

Color removal efficiencies for catalyst composites are measured via ultraviolet adsorption at 340 nm. In one embodiment, the catalyst composites of the present invention remove at least about 75% of color from crude terephthalic acid. In another embodiment, the catalyst composites of the present invention remove at least about 80% of color from crude terephthalic acid. In yet another embodiment, the catalyst composites of the present invention remove at least about 90% of color from crude terephthalic acid.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A catalyst composite comprising:
   an extruded catalyst support comprising an extruded activated carbonaceous material having pores and wherein at least about 40% of total Hg porosity occurs in pores having a diameter of about 200 Å and larger; and
   a precious metal catalyst.

2. A catalyst composite comprising:
   an extruded catalyst support comprising an extruded activated carbonaceous material having pores and wherein at least about 38% of total Hg porosity occurs in pores having a diameter of about 1,000 Å and larger; and
   a precious metal catalyst.

3. A catalyst composite comprising:
   an extruded catalyst support comprising an extruded activated carbonaceous material having pores and wherein at least about 34% of total Hg porosity occurs in pores having a diameter of about 5,000 Å and larger; and
   a precious metal catalyst.

4. The catalyst composite according to claim 3, wherein the catalyst composite comprises about 70% by weight or more and about 99.99% by weight or less of the extruded catalyst support and about 0.01% by weight or more and about 30% by weight or less of the precious metal catalyst.

5. A catalyst composite comprising:
   an extruded activated carbonaceous material comprising a first set of pores having a pore diameter of at least about 40 Å and at most about 100 Å with a porosity of at least about 0.15 cc/g, and a second set of pores having a pore diameter of at least about 5,000 Å and at most about 20,000 Å with a porosity of at least about 0.3 cc/g; and
   a precious metal catalyst.

6. The catalyst composite according to claim 5, wherein at least about 40% of total Hg porosity occurs in a third set of pores having a diameter of about 200 Å and larger in the extruded activated carbonaceous material.

7. The catalyst composite according to claim 5, wherein the catalyst composite comprises about 70% by weight or more and about 99.99% by weight or less of the extruded activated carbonaceous material and about 0.01% by weight or more and about 30% by weight or less of the precious metal catalyst.

8. The catalyst composite according to claim 5, wherein the catalyst composite is at least one of a hydrogenation catalyst composite, a rearrangement catalyst composite, a purification catalyst composite, a dehydration catalyst composite, a dehydrogenation catalyst composite, an oxidation catalyst composite, a reduction catalyst composite, a polymerization catalyst composite, a dehydrocyclization catalyst composite, a reforming catalyst composite, a hydrocracking catalyst composite, and an isomerization catalyst composite.

9. The catalyst composite according to claim 5, wherein the precious metal catalyst comprises at least one selected from the group of platinum, platinum and rhenium, platinum and ruthenium, platinum and tungsten, platinum and nickel, platinum and tin, platinum and iron, platinum and copper, platinum and rhodium, platinum and lead, platinum and germanium, palladium, palladium and rhenium, platinum and gold, platinum and tellurium, palladium and gold, palladium and indium, palladium and sulfur, palladium and tellurium, palladium and rhodium, palladium and tungsten, palladium and nickel, palladium and tin, palladium and copper, palladium and ruthenium, palladium and lead, palladium and germanium, cobalt, rhodium, ruthenium, osmium, and iridium.

10. The catalyst composite according to claim 5, wherein the extruded activated carbonaceous material comprises a first set of pores having a pore diameter of at least about 40 Å and at most about 100 Å with a porosity of at least about 0.2 cc/g, and a second set of pores having a pore diameter of at least about 5,000 Å and at most about 20,000 Å with a porosity of at least about 0.4 cc/g.

11. The catalyst composite according to claim 5, wherein at least about 38% of total Hg porosity occurs in a third set of pores having a diameter of about 1,000 Å and larger in the extruded activated carbonaceous material.

12. A method of making a catalyst composite:
   mixing at least one carbonaceous material and a liquid to form a mixture;
   extruding the mixture into a shaped material;
   optionally drying the shaped material;
   heat treating the shaped material at a temperature from about 600° C. to about 1,500° C. to provide a catalyst support, wherein the catalyst support has at least about 40% of total Hg porosity in pores having a diameter of about 200 Å and larger; and
   contacting a precious metal catalyst with the catalyst support.

13. The method according to claim 12, wherein the catalyst support comprises a set of pores having a pore diameter of at least about 40 Å and at most about 100 Å with a porosity of at least about 0.15 cc/g, and another set of pores having a pore diameter of at least about 5,000 Å and at most about 20,000 Å with a porosity of at least about 0.3 cc/g.

14. The method according to claim 12, wherein the shaped material is in the form of one or more from the group consisting of spheres, tablets, cylinders, stars, tri-lobes, quadra-lobes, pellets, granules, honeycombs, and cubes.

15. The method according to claim 12, wherein the shaped material comprises less than about 3% by weight free moisture.

16. The method according to claim 12, wherein mixing is conducted for a time of about 5 minutes or more and about 100 minutes or less and the shaped material is heat treated at a temperature from about 700° C. to about 1,000° C.

17. A catalyst composite comprising:
   an extruded catalyst support comprising an extruded activated carbonaceous material having pores and wherein at least about 40% of total Hg porosity occurs in pores having a diameter of about 1,000 Å and larger; and
   a precious metal catalyst.

18. The catalyst composite according to claim 17, wherein the catalyst composite comprises about 70% by weight or more and about 99.99% by weight or less of the extruded catalyst support and about 0.01% by weight or more and about 30% by weight or less of the precious metal catalyst.

19. The catalyst composite according to claim 17, wherein the catalyst composite is at least one of a hydrogenation catalyst composite, a rearrangement catalyst composite, a purification catalyst composite, a dehydration catalyst composite, a dehydrogenation catalyst composite, an oxidation catalyst composite, a reduction catalyst composite, a polymerization catalyst composite, a dehydrocyclization catalyst composite, a reforming catalyst composite, a hydrocracking catalyst composite, and an isomerization catalyst composite.

20. The catalyst composite according to claim 17, wherein the precious metal catalyst comprises at least one selected from the group of platinum, platinum and rhenium, platinum and ruthenium, platinum and tungsten, platinum and nickel, platinum and tin, platinum and iron, platinum and copper, platinum and rhodium, platinum and lead, platinum and germanium, palladium, palladium and rhenium, platinum and gold, platinum and tellurium, palladium and gold, palladium and indium, palladium and sulfur, palladium and tellurium, palladium and rhodium, palladium and tungsten, palladium and nickel, palladium and tin, palladium and copper, palladium and ruthenium, palladium and lead, palladium and germanium, cobalt, rhodium, ruthenium, osmium, and iridium.

21. A catalyst composite comprising:
    an extruded activated carbonaceous material comprising a first set of pores having a pore diameter of at least about 40 Å and at most about 100 Å with a porosity of at least about 0.2 cc/g, and a second set of pores having a pore diameter of at least about 5,000 Å and at most about 20,000 Å with a porosity of at least about 0.4 cc/g; and
    a precious metal catalyst.

22. The catalyst composite according to claim 21, wherein the catalyst composite comprises about 70% by weight or more and about 99.99% by weight or less of the extruded activated carbonaceous material and about 0.01% by weight or more and about 30% by weight or less of the precious metal catalyst.

23. The catalyst composite according to claim 21, wherein the catalyst composite is at least one of a hydrogenation catalyst composite, a rearrangement catalyst composite, a purification catalyst composite, a dehydration catalyst composite, a dehydrogenation catalyst composite, an oxidation catalyst composite, a reduction catalyst composite, a polymerization catalyst composite, a dehydrocyclization catalyst composite, a reforming catalyst composite, a hydrocracking catalyst composite, and an isomerization catalyst composite.

24. The catalyst composite according to claim 21, wherein the precious metal catalyst comprises at least one selected from the group of platinum, platinum and rhenium, platinum and ruthenium, platinum and tungsten, platinum and nickel, platinum and tin, platinum and iron, platinum and copper, platinum and rhodium, platinum and lead, platinum and germanium, palladium, palladium and rhenium, platinum and gold, platinum and tellurium, palladium and gold, palladium and indium, palladium and sulfur, palladium and tellurium, palladium and rhodium, palladium and tungsten, palladium and nickel, palladium and tin, palladium and copper, palladium and ruthenium, palladium and lead, palladium and germanium, cobalt, rhodium, ruthenium, osmium, and iridium.

25. A method of making a catalyst composite:
    mixing at least one carbonaceous material and a liquid to form a mixture;
    extruding the mixture into a shaped material;
    optionally drying the shaped material;
    heat treating the shaped material at a temperature from about 600° C. to about 1,500° C. in an atmosphere comprising steam and at least one of an inert gas, air, oxygen, and carbon dioxide to provide a catalyst support, wherein the catalyst support has at least about 40% of total Hg porosity in pores having a diameter of about 200 Å and larger; and
    contacting a precious metal catalyst with the catalyst support.

26. The method according to claim 25, wherein the catalyst support comprises a set of pores having a pore diameter of at least about 40 Å and at most about 100 Å with a porosity of at least about 0.15 cc/g, and another set of pores having a pore diameter of at least about 5,000 Å and at most about 20,000 Å with a porosity of at least about 0.3 cc/g.

27. The method according to claim 25, wherein the shaped material is in the form of one or more from the group consisting of spheres, tablets, cylinders, stars, tri-lobes, quadra-lobes, pellets, granules, honeycombs, and cubes.

28. The method according to claim 25, wherein mixing is conducted for a time of about 5 minutes or more and about 100 minutes or less and the shaped material is heat treated at a temperature from about 700° C. to about 1,000° C.

* * * * *